(12) United States Patent
Gasper

(10) Patent No.: US 6,260,969 B1
(45) Date of Patent: Jul. 17, 2001

(54) MAGNIFICATION TEST APPARATUS

(75) Inventor: Carlisle Charles Frederick Gasper, Glenn Iris (AU)

(73) Assignee: Carl Gasper & Associated Pty. Ltd., Glen Iris (AU)

( * ) Notice: Subject to any disclaimer, the term of this patent is extended or adjusted under 35 U.S.C. 154(b) by 0 days.

(21) Appl. No.: 09/554,826
(22) PCT Filed: Nov. 19, 1998
(86) PCT No.: PCT/AU98/00964
§ 371 Date: Sep. 14, 2000
§ 102(e) Date: Sep. 14, 2000
(87) PCT Pub. No.: WO99/26525
PCT Pub. Date: Jun. 3, 1999

(30) Foreign Application Priority Data

Nov. 19, 1997 (AU) .................................................. PP 0469

(51) Int. Cl.⁷ ....................................................... A61B 3/02
(52) U.S. Cl. ............................................................. 351/223
(58) Field of Search ..................................... 351/216, 217, 351/218, 222, 223, 227, 229, 230, 231, 233, 235, 245

(56) References Cited

U.S. PATENT DOCUMENTS

| | | | |
|---|---|---|---|
| 1,437,776 | * 12/1922 | Reese et al. | ........................ 351/223 |
| 5,486,879 | * 1/1996 | Barnett | ................................. 351/223 |
| 5,861,941 | * 1/1999 | Leibars et al. | ....................... 351/245 |

\* cited by examiner

Primary Examiner—George Manuel
(74) Attorney, Agent, or Firm—James Ray & Associates

(57) ABSTRACT

A magnification testing apparatus for testing the suitability of eyeglasses is disclosed. The apparatus includes a plurality of frames for eyeglass lenses, a plurality of pairs of lenses of different magnification secured within the frames, a support means holding the frames for a user of the apparatus to position their face so as to bring each of the frames in turn into a conventional eyeglass-wearing position, and a motif of a first predetermined size that is spaced in use of the apparatus a first predetermined distance from each frame when each frame is in the conventional eyeglass-wearing position.

17 Claims, 3 Drawing Sheets

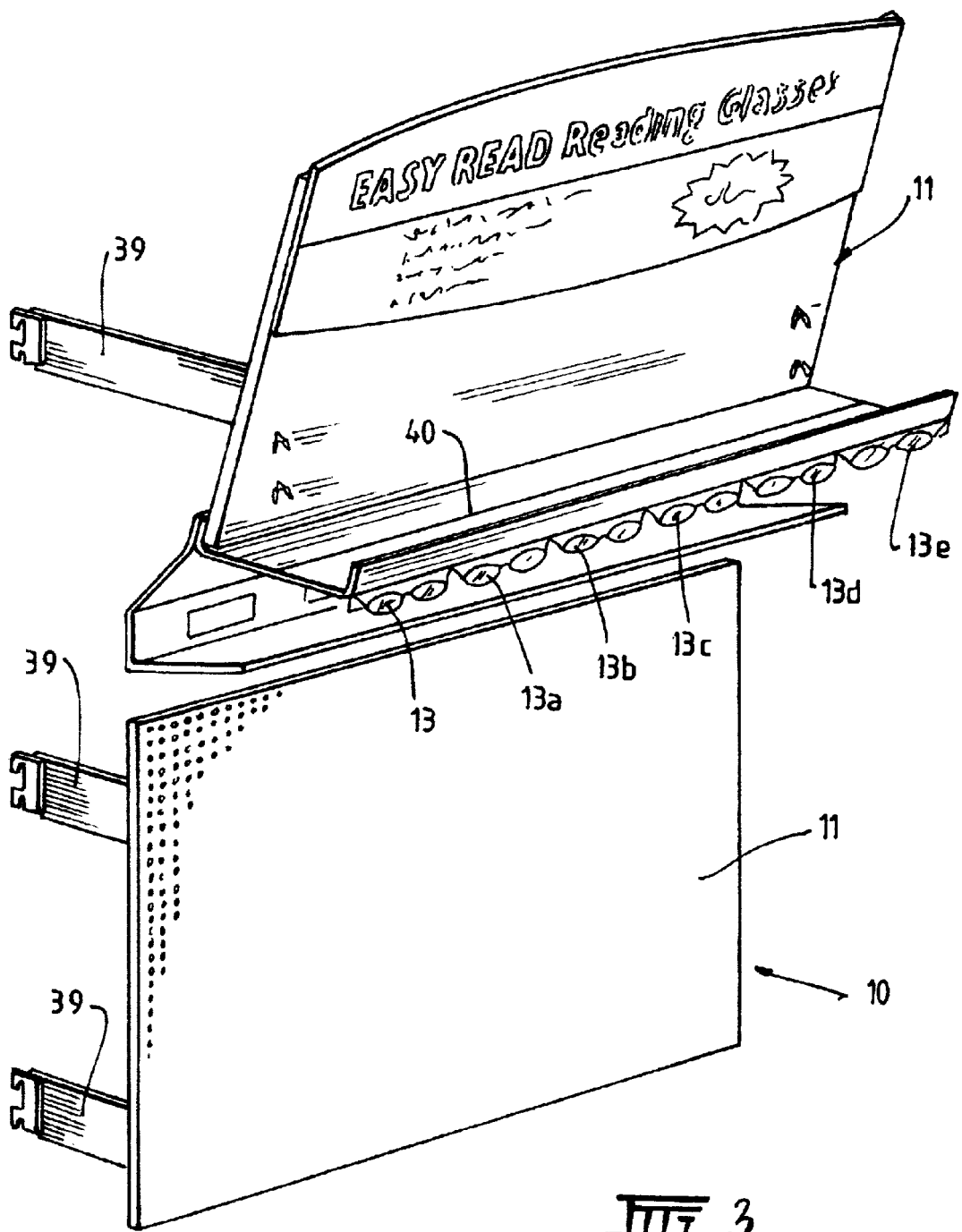

MAGNIFICATION TEST APPARATUS

The present invention is concerned with a magnification test apparatus for eyeglasses and, more particularly, with a magnification test apparatus for reading glasses.

With advancing age, many people progressively become long-sighted. This condition can easily be corrected by the provision of reading glasses, which serve to magnify images (such as print) held only a short distance from the face of a person which would otherwise be too small to view properly. The magnification required is different for different people. Moreover, as the condition of a person's vision changes over time, the magnification required will alter.

There are two options for people to obtain reading glasses. The first, more conventional option, of attending on optometrist and being tested and prescribed optical lenses is not always an affordable or readily or conveniently accessible option. The second option of a person purchasing from a retail outlet one pair of reading glasses from a group of reading glasses having a range of particular magnifications overcomes the disadvantages of the first option but has the disadvantage that it is not always a straight-forward exercise to select an appropriate magnification.

The usual means of testing reading glasses in the "self-service" option is to pick up a loose pair of glasses, try them on and then attempt to read some nearby print. The conditions of such a test are not sufficiently well-controlled to allow for adequate testing of the glasses, and glasses with an inappropriate magnification are sometimes chosen as a result.

The present invention allows for testing of glasses under controlled conditions in a "self-service" situation.

In general terms the present invention provides a magnification testing apparatus for testing the suitability of eyeglasses, which apparatus includes:

(a) a plurality of frames for eyeglass lenses;

(b) a plurality of pairs of lenses of different magnification secured within the frames;

(c) a support means holding the frames for a user of the apparatus to position their face so as to bring each of the frames in turn into a conventional eyeglass-wearing position; and (d) a motif of a first predetermined size spaced a first predetermined distance from each frame when the frame is in the conventional eyeglass-wearing position.

The frames may be arranged in a line. With this arrangement preferably there is a motif aligned with each frame.

Alternatively the frames may be arranged in a circular array on a turret that can be rotated about a vertical axis. With this arrangement preferably there is a single fixed motif and the frames can be rotated successively into a viewing position in relation to the motif.

More particularly, according to the present invention there is provided a magnification testing apparatus for testing the suitability of eyeglasses, which includes:

(a) a first frame for eyeglass lenses;

(b) a second frame for eyeglass lenses;

(c) a support means holding the frames for a user of the apparatus to position their face so as to being each of the frames in turn into a conventional eyeglass-wearing position;

(d) a first pair of lenses secured within the first frame, the first pair of lenses possessing predetermined optical properties;

(e) a second pair of lenses secured within the second frame, the second pair of lenses possessing predetermined optical properties.

(f) a first motif of a first predetermined size spaced apart from the first frame by a first predetermined distance; and (g) a second motif of a second predetermined size spaced apart from the second frame by a second predetermined distance.

In one embodiment the first and second predetermined distances are the same distance, the first and second motifs are the same size, and the first and second pairs of lenses have different magnifications.

In another embodiment, the first and second predetermined distances are not identical.

With this embodiment one of the first and second motifs may be scaled up or down in size by the appropriate amount to compensate for the different viewing distances.

Alternatively, or in addition, the first and second pairs of lenses may have different magnifications.

Preferably, the first and second motifs are identical to allow for easy comparison.

Typically, each of the first and second motifs is a passage of print that is too small to be read by a person requiring reading glasses at the first or second predetermined distance chosen. In general this distance is 30–35 cm, to stimulate usual reading conditions.

Preferably, the first pair of lenses and the second pair of lenses are the lenses of conventional reading glasses.

Preferably, the first pair of lenses has a different magnification to the second pair of lenses. In general, a plurality of such lenses are arranged in the magnification testing apparatus described above so that a user of the apparatus can try a large range of lenses and make a direct comparison of the suitability of the magnification levels of the lenses.

For convenience, the support means can be a display unit with reading glasses displayed thereon.

Preferably, a plurality of pairs of lenses are arranged in a row positioned towards the top of the display unit and reading glasses having the same magnification as a particular pair of lenses are displayed directly beneath it.

The display unit may include a mirror positioned above the frames so that the user of the apparatus can also check their appearance while the frames are in the conventional eyeglass-wearing position. The mirror may be angled, say at 20° to the vertical, to facilitate viewing and frames of different styles (as well as different magnifications) may be displayed.

Preferably the display unit includes one or more than one member, such as a rod or any other suitable means, on which each frame is mounted.

Preferably the frames, which do not have the "arms" used to secure eyeglasses on the head of a wearer, are suspended by the member or members in positions to which a user of the apparatus can readily position their head to assess whether the pairs of lenses have the correct magnification.

For convenience, preferably the frames are located between 900 mm and 1 m above the floor, as it has been found that bending to this height is most comfortable for the majority of people.

Alternatively, the frames are mounted in a surface of the support means or extending from the support means. This surface may be shaped to allow for comfortable positioning of the face of the user.

Preferred embodiments of the invention will now be described, by way of example only, with reference to the accompanying drawings, of which:

FIG. 3 is a perspective view of another embodiment of a magnification test apparatus in accordance with the present invention.

Figure 1:
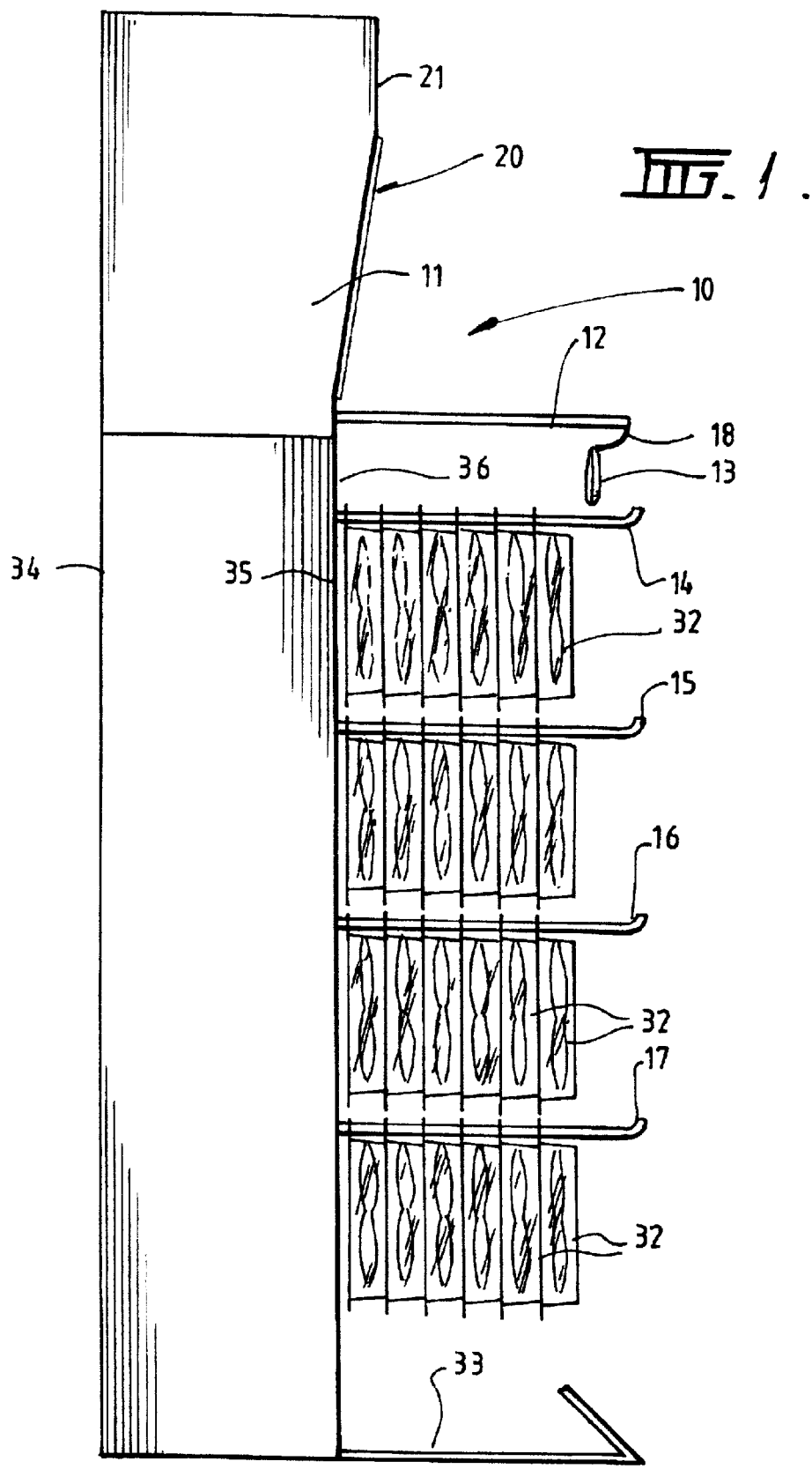
FIG. 1 is a side elevation of one embodiment of a magnification test apparatus in accordance with the present invention.
Figure 2:
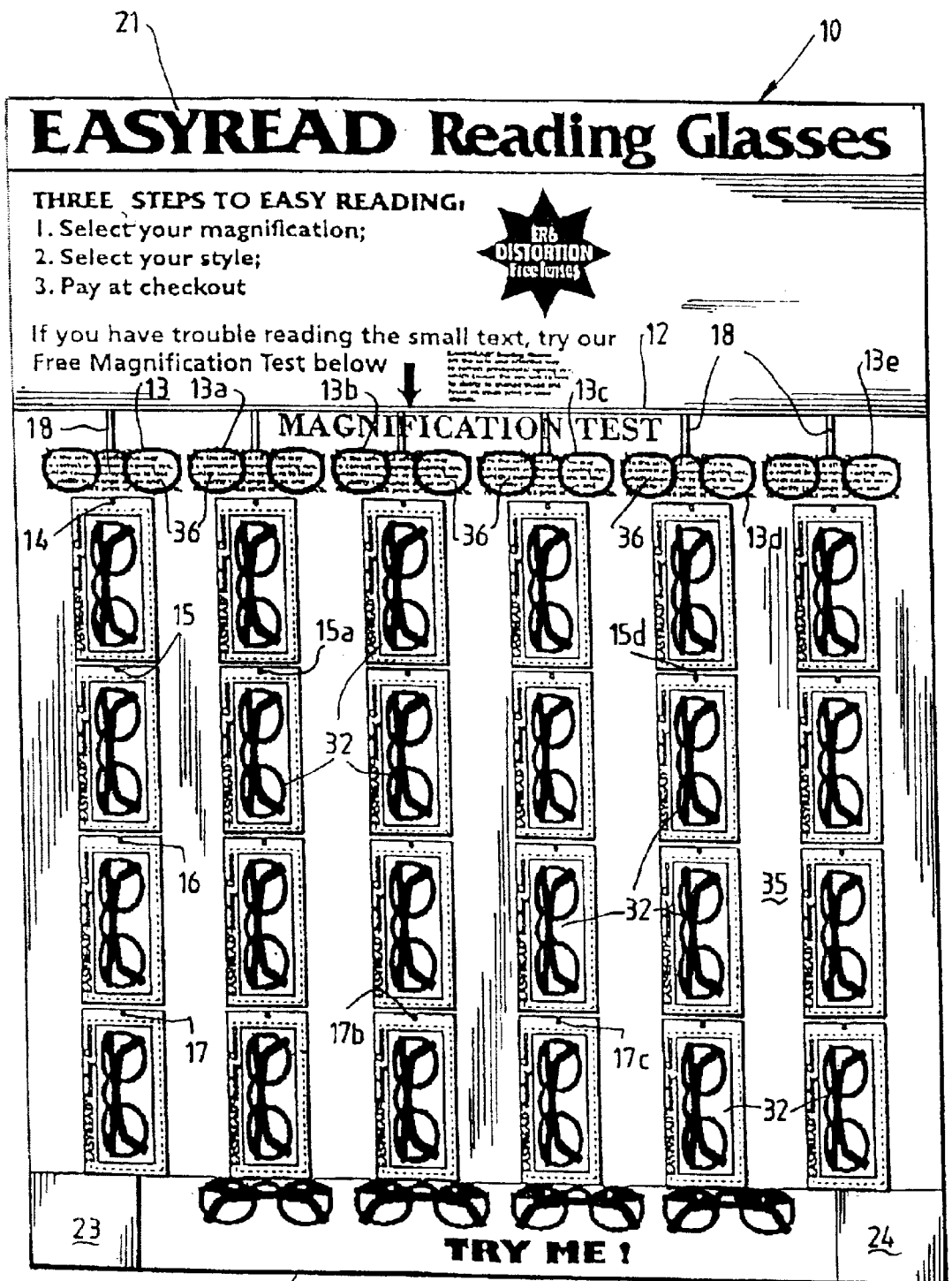
FIG. 2 is a partially schematic front elevation of the magnification test apparatus shown in FIG. 1.

The apparatus 10 shown in FIGS. 1 and 2 includes:

(a) a support means, in this case a free-standing display unit 11 with a base 33, an upright wall section 34, and a front face section 35;

(b) a plurality of test eyeglasses 13, 13a, 13b, 13c, 13d, 13e each of which includes a frame and a pair of lenses (hereinafter referred to as a "test frame") arranged in a horizontal line;

(c) a plurality of members, such as rod 12, which support the test frames 13–13e in the line; and (d) an array of pegs, such as pegs 14, 15, 16, 17, which support and thereby display reading glasses 32 packaged in blister packs.

The reading glasses 32 are suspended from the pegs in a conventional manner directly beneath the test frame 13–13e having the same magnification.

It will be appreciated that the shape and position of each rod 12, particularly in relation to the upper pegs 14, is selected so that the user of the apparatus can press their face against the test frames 13–13e to bring the test frames into the usual eyeglass-wearing position within interference from other components of the apparatus 10, such as the pegs 14. Each test frame 13–13e includes a loop 18 that extends from the end of a rod 12 to the nose bridge of the test frames 13–13e. The loop 18 and the bridge of each test frame 13–13e are arranged so as to securely hold the test frames 13–13e while not preventing the user of the apparatus from positioning their face appropriately and in comfort.

The apparatus 10 further includes a motif 36 associated with each test frame 13–13e positioned on the front face section 35 of the display unit 11. Each motif 36 is positioned in the line of sight for its associated test frames 13–13e.

The display unit 11 also includes a mirror 20 located just above the test frames 13–13e and extending substantially the width of the display unit 11. The mirror 20 allows users of the apparatus 10 to view the test frames 13–13e when in the eyeglass-wearing position so as to judge the style of the glasses. Different styles of glasses with the same magnification may be positioned side-by-side, with groups of various styles each with the same magnification being created. The mirror is angled at 20° of the vertical so that a person bent over the apparatus and in the eyeglass-wearing position can better see themselves.

A header section 21 of the front face section 35 of the display unit 11 may bear explanatory text and/or advertising as best seen in FIG. 2. In this embodiment of the invention the mirror 20 is not included and the representation of the apparatus 10 is partially schematic, however the concept of the invention is illustrated.

Following the instructions on the header 21, a user of the apparatus 10 selects first the test frame 13 and views the print of the aligned motif 36 by looking through the test frame 13, in the manner described previously, by placing their face in the eyeglass-wearing position against the test frame 13. The user judges whether they can read the print adequately. If not, they select another test frame 13a and judge whether they can read the text of the associated motif 36 and so on with the remainder of the test frames 13b, 13c, 13d, 13e.

The size of the print of each motif is the same (in fact the print is identical) but the magnification of the lenses in the test frames 13–13e increases progressively from the first frame 13 to the last frame 13e in the line.

A person requiring only weak reading glasses may find that the print is clearest when using frame 13 or 13a but a person requiring strong reading glasses may not be satisfied until they have read the print through frame 13d or 13e. Thus, the user of the apparatus 10 self-selects the most appropriate level of magnification for their reading glasses under controlled conditions that allow for an appropriate selection.

Then, for the convenience of the user, packaged reading glasses with the same level of magnification are displayed beneath each test frame 13a–13e. Thus, the reading glasses with the lowest level of magnification are displayed on pegs 14, 15, 16, 17 beneath test frame 13, those with the next lowest level of magnification on pegs 14a, 15 16a, 17a, beneath test frame 13a, and so on. Typically the reading glasses in each column are packed in blister packs that hang from the pegs, and are spaced by only 5 mm to maximize the use of space in the display unit 11. Information leaflets may also be displayed in pockets 23, 24.

The apparatus 10 shown in FIG. 3 is similar conceptually to that shown in FIGS. 1 and 2. The same reference numerals are used to denote the same components of each apparatus. In addition, the display pegs 14, 15, 16, 17 and blister packs of reading glasses have been removed for clarity.

One difference between the apparatus 10 shown in FIG. 3 and that shown in FIGS. 1 and 2 is that the apparatus shown in FIGS. 3 does not include a free-standing display unit 11 but rather includes support members 39 which enables the display unit 11 to be wall mounted.

Another difference is that the display unit 11 shown in FIG. 3 includes a display shelf 40 and the test frames 13a–13e are supported by a shelf 40 that forms part of the display unit 11.

Variations and modifications apparent to those skilled in the art are encompassed within the above description of the invention.

By way of example, whilst the preferred embodiments described above include test frames 13–13e which have different magnifications, it can readily be appreciated that the present invention is not restricted to this arrangement and extends to arrangements in which the test frames have the same magnification and there are different spacings between each test frame and the motifs 36 and/or different sized motifs 36.

In summary, the present invention extends to any arrangement in which the parameters of magnification, motif size, and spacing between test frames and motifs are selected so that users can use the apparatus of the present invention to assess, in effect, different magnification eyeglasses.

By way of further example, whilst the preferred embodiments described above include test frames 13–13e which are arranged in a line and separate albeit identical motifs 36 which are aligned with each test frame, it can readily be appreciated that the present invention is not so limited and extends to arrangements in which the test frames 13–13e are in a circular array on a turret that can be rotated about a vertical axis to bring each test frame in turn into alignment with a single fixed motif.

What is claimed is:

1. A magnification testing apparatus for testing the suitability of eyeglasses, which includes:

(a) a first frame for eyeglass lenses;

(b) a second frame for eyeglass lenses;

(c) a support means holding the frames for a user of the apparatus to position their face so as to bring each of the frames in turn into a conventional eyeglass-wearing position;

(d) a first pair of lenses secured within said first frame, said first pair of lenses possessing predetermined optical properties;

(e) a second pair of lenses secured within said second frame, said second pair of lenses possessing predetermined optical properties;

(f) a first motif of a first predetermined size spaced apart from said first frame by a first predetermined distance; and (g) a second motif of a second predetermined size spaced apart from said second frame by a second predetermined distance.

2. The apparatus defined in claim 1 wherein the first and second predetermined distances are the same distance, the first and second motifs are the same size, and the first and second pairs of lenses have different magnifications.

3. The apparatus defined in claim 1 wherein the first and second predetermined distances are not identical.

4. The apparatus defined in claim 3 wherein one of said first and second motifs is scaled up or down in size by an appropriate amount to compensate for the different viewing distances.

5. The apparatus defined in claim 4 wherein the first and second pairs of lenses have different magnifications.

6. The apparatus defined in claim 3 wherein the first and second pairs of lenses have different magnifications.

7. The apparatus defined in claim 3 wherein the first and second pairs of lenses have the same magnification.

8. The apparatus defined in claim 1 wherein the first and second motifs are identical to allow for easy comparison.

9. The apparatus defined in claim 1 wherein the first and second motifs are both a passage of print, too small to be read by a person requiring reading glasses at the predetermined distance chosen.

10. The apparatus defined in claim 1 wherein the first and second predetermined distances are 30–35 cm to stimulate usual reading conditions.

11. The apparatus defined in claim 1 wherein the first and second pairs of lenses are the lenses of conventional reading glasses.

12. The apparatus defined in claim 1 wherein the support means is a display unit with reading glasses packaged for retail sale displayed thereon.

13. A magnification testing apparatus for testing the suitability of eyeglasses, which apparatus includes:

(a) a plurality of frames for eyeglass lenses;

(b) a plurality of pairs of lenses of different magnification secured within the frames;

(c) a support means holding the frames for a user of the apparatus to position their face so as to bring each of the frame in turn into a conventional eyeglass-wearing position; and (d) a motif of a first predetermined size that is spaced in use of the apparatus a first predetermined distance from each frame when each frame is in the conventional eyeglass-wearing position.

14. The apparatus defined in claim 13 wherein the frames are arranged in a line.

15. The apparatus defined in claim 14 wherein one said motif is aligned with each frame.

16. The apparatus defined in claim 14 wherein the frames are arranged in a circular array on a turret that can be rotated about a vertical axis.

17. The apparatus defined in claim 16 wherein there is a single said motif and the frames can be rotated successively into a viewing position in relation to the motif.

\* \* \* \* \*